US006596926B1

(12) United States Patent
Famodu et al.

(10) Patent No.: US 6,596,926 B1
(45) Date of Patent: Jul. 22, 2003

(54) PHOSPHATIDYLCHOLINE BIOSYNTHETIC ENZYMES

(75) Inventors: Omolayo O. Famodu, Newark, DE (US); Anthony J. Kinney, Wilmington, DE (US); J. Antoni Rafalski, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/668,262

(22) Filed: Sep. 22, 2000

Related U.S. Application Data

(60) Provisional application No. 60/155,626, filed on Sep. 23, 1999.

(51) Int. Cl.$^7$ .......................... A01H 3/00; C07H 21/04; C07K 14/415; C12N 5/14; C12N 9/00
(52) U.S. Cl. .......................... 800/281; 435/6; 435/69.1; 435/183; 435/410; 435/419; 435/252.3; 435/320.1; 530/350; 530/370; 536/23.2; 536/23.6; 536/24.1; 536/24.3; 536/24.33; 800/278; 800/295
(58) Field of Search .......................... 435/6, 69.1, 183, 435/410, 419, 252.3, 320.1; 530/350, 370; 536/23.2, 23.6, 24.1, 24.3, 24.33; 800/278, 295, 281

(56) References Cited

PUBLICATIONS

Michael J. Homann et al., Journal of Bacteriology, vol. 169(7):3276–3280, Jul. 1987, Coordinate Regulation of Phospholipid Biosynthesis by Serine in *Saccharomyces cerevisiae*.

Xiaoying Lin et al., Nature, vol. 402:761–768, Dec. 16, 1999, Sequence and Analysis of Chromosome 2 of the plant *Arabidopsis thaliana*.

Patricia McGraw et al., Genetics, vol. 122:317–330, Jun. 1989, Mutations in the *Saccharomyces cerevisiae* opi3 Gene: Effects on Phospholipid Methylation, Growth and Cross–Pathway Regulation of Inositiol Synthesis.

National Center for Biotechnology Information General Identifier No. 3786005, Apr. 5, 2000, Lin, X. et al., Sequence and Analysis of Chromosome 2 of the plant *Arabidopsis thaliana*.

National Center for Biotechnology Information General Identifier No. 4505651, Oct. 31, 2000, Nakashima, A. et al., Cloning of a human cDNA for CTP–phosphoethanolamine Cytidylyltransferase by Complementation in vivo of a yeast mutant.

Asae Nakashima et al., Journ. of Biol. Chem., vol. 272(14):9567–9572, Apr. 4, 1997, Cloning of a human cDNA for CTP–phosphoethanolomine Cytidylyltransferase by Complementation in vivo of a yeast mutant.

National Center for Biotechnology Information General Identifier No. 3396102,, Oct. 21, 1999, Bladergroen, B. A. et al., Cloning and Expression of CTP: phosphoethanolamine cytidylyltransferase cDNA from rate liver.

Bellinda A. Bladergroen et al., Biochem. J., vol. 343:107–114, 1999, Cloning and Expression of CTP: phosphoethanolamine cytidylyltransferase cDNA from rate liver.

National Center for Biotechnology Information General Identifier No. 7298016, Oct. 4, 2000, Adams, M. D. et al., The Genome Sequence of *Drosophila melanogaster*.

Mark D. Adams et al., Science, vol. 287:2185–2195, Mar. 24, 2000, The Genome Sequence of *Drosophila melanogaster*.

National Center for Biotechnology Information General Identifier No. 6012413, Oct. 5, 1999, Walbot, V., Maize ESTs from Various cDNA Libraries sequenced at Stanford University.

National Center for Biotechnology Information General Identifier No. 3760654, Oct. 19, 1998, Sasaki, T. et al., Rice cDNA from Callus.

National Center for Biotechnology Information General Identifier No. 7285973, Mar. 22, 2000, Shoemaker, R. et al., Public Soybean EST Project.

National Center for Biotechnology Information General Identifier No. 5459516, Jul. 13, 1999, Maeda, E. et al., *Homo sapiens* phosphatidylethanolamine N–methyltransferase mRNA, complete.

National Center for Biotechnology Information General Identifier No. 6322533, Jan. 5, 2001, Galibert, F. et al., Complete Nucleotide Sequence of *Saccharomyces cerevisiae* Chromosome X.

F. Galibert et al., EMBO J., vol. 15(9):2031–2049, 1996, Complete Nucleotide Sequence of *Saccharomyces cerevisiae* Chromosome X.

A. Goffeau et al., Science, vol. 274:546–567, Oct. 25, 1996, Life with 6000 Genes.

Roger Sundler, Journ. of Biol. Chem., vol. 250(22):8585–8590, Nov. 25, 1975, Ethanolaminephosphate Cytidylyltransferase.

Dennis E. Vance et al., Methods in enzymology, vol. 70:581–588, 1981, Conversion of Phosphatidylethanolamine to Phosphatidylcholine.

Margaret I. Kanipes et al., Biochimica et Biophysica Acta vol. 1348:134–141, 1997, The phospholipid methyltransferases in yeast.

Lazar et al. Molecular and Cellular Biology, Mar. 1988, vol. 8, No. 3, p. 1247–1252.*

Burgess et al. The Journal of Cell Biology, 1990, vol. 111, p. 2129–2138.*

Brown et al. Science, Nov. 13, 1998, vol. 282, p. 131–133.*

Bork. Genome Research, vol. 10, 2000, p. 398–400.*

\* cited by examiner

*Primary Examiner*—Phuong T. Bui

(57) ABSTRACT

This invention relates to an isolated nucleic acid fragment encoding phosphatidylethanolamine N-methyltransferase biosynthetic enzyme. The invention also relates to the construction of a chimeric gene encoding all or a portion of the phosphatidylethanolamine N-methyltransferase biosynthetic enzyme, in sense or antisense orientation, wherein expression of the chimeric gene results in production of altered levels of phosphatidylethanolamine N-methyltransferase biosynthetic enzyme in a transformed host cell.

13 Claims, No Drawings

PHOSPHATIDYLCHOLINE BIOSYNTHETIC ENZYMES

This application claims the benefit of U.S. Provisional Application No. 60/155,626, filed Sep. 23, 1999.

FIELD OF THE INVENTION

This invention is in the field of plant molecular biology. More specifically, this invention pertains to nucleic acid fragments encoding phosphatidylcholine biosynthetic enzymes in plants and seeds.

BACKGROUND OF THE INVENTION

Phosphatidylcholine (PC), phosphatidylethanolamine (PE), phosphatidylserine (PS), phosphatidylinositol (PI), phosphatidylglycerol (PG) and diphosphatidylglycerol (DPG) are the major phospholipids found in plant tissues. The distribution of these lipids among the various organelles of different tissues and among different plants has been comprehensively studied. The pathways by which these lipids are synthesized have also been studied extensively but very few of the plant enzymes involved in these pathways have been purified or their corresponding genes cloned.

The precursor molecule common to the de novo synthesis of all phospholipids in prokaryotes and eukaryotes is phosphatidic acid (PA). Synthesis of PA occurs by the sequential acylation of glycerol-3-phosphate by glycerol-3-phosphate acyltransferase and 1-monoacylglycerol-3-phosphate acyltransferase, both of which utilize acyl-CoA as a source of acyl moieties. PA may be converted to CDP-diacylglycerol by the action of the enzyme CDP-diacylglycerol synthase (E.C. 2.7.7.41; also called CTP: phosphatidate cytidylyltransferase, phosphate cytidylyltransferase, phosphoethanolamine cytidylyltransferase, among others). This enzyme has been characterized in yeast where it has been demonstrated to be highly regulated (Homann et al. (1987) *J. Bacteriol.* 169:3276–3280). While phosphatidate cytidylyltransferase activity has been detected in the chloroplast, mitochondria and microsomes of several plants, no sequence information of plant phosphatidate cytidylyltransferase has been confirmed. The sequence of an *Arabidopsis thaliana* putative phosphoethanolamine cytidylyltransferase was identified when the sequence of the chromosome 2 was determined (Lin et al. (1999) *Nature 402:761–768*).

In castor bean endosperms PE is sequentially methylated to PC by methyltransferases which utilize S-adenosylmethionine as the methyl donor. PE N-methyltransferase (EC 2.1.1.17) catalyzes the methylation of PE to phosphatidyl methylethanolamine (PME) and phosphatidyl-N-methylethanolamine N-methyltransferase (EC 2.1.1.71; also called phosphatidylethanolamine N-methyltransferase) catalyzes the two methylations necessary to convert PME to PC (McGraw and Henry (1989) *Genetics* 122:317–330). The sequence of a plant phosphatidylethanolamine N-methyltransferase has yet to be determined.

Identification of the sequences encoding phosphoethanolamine cytidylyltransferase or phosphatidylethanolamine N-methyltransferase in plants will allow the manipulation of these genes in transgenic plants.

SUMMARY OF THE INVENTION

The present invention concerns an isolated polynucleotide comprising a nucleotide sequence selected from the group consisting of: (a) a first nucleotide sequence encoding a polypeptide of at least 40 amino acids having at least 80% identity based on the Clustal method of alignment when compared to a polypeptide selected from the group consisting of SEQ ID NOs:2, 4, 6, 8, 10, 18, and 20, (b) a second nucleotide sequence encoding a polypeptide of at least 200 amino acids having at least 80% identity based on the Clustal method of alignment when compared to a polypeptide selected from the group consisting of SEQ ID NOs:12, 14, and 18, and (c) a third nucleotide sequence comprising the complement of the first or second nucleotide sequences.

In a second embodiment, it is preferred that the isolated polynucleotide of the claimed invention comprises nucleotide sequence selected from: (a) a first nucleotide sequence of at least 100 nucleotides having at least 80% identity based on the Clustal method of alignment when compared to a nucleotide sequence selected from SEQ ID NOs:1, 3, 5, 7, 9, 17, and 19, and (b) a second nucleotide sequence selected from the group consisting of SEQ ID NOs:11, 13, and 15.

In a third embodiment, this invention concerns an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, and 19 and the complement of such nucleotide sequences.

In a fourth embodiment, this invention relates to a chimeric gene comprising an isolated polynucleotide of the present invention operably linked to at least one suitable regulatory sequence.

In a fifth embodiment, the present invention concerns an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

In a sixth embodiment, the invention also relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

In a seventh embodiment, the invention concerns a CTP: phosphoethanolamine cytidylyltransferase or a phosphatidylethanolamine N-methyltransferase polypeptide selected from the group consisting of (a) a first polypeptide of at least 40 amino acids comprising at least 80% identity based on the Clustal method of alignment compared to a polypeptide selected from SEQ ID NOs:2, 4, 6, 8, 10, 18, and 20, and (b) a second polynucleotide of at least 200 amino acids comprising at least 80% identity based on the Clustal method of alignment compared to a polypeptide selected from the group consisting of SEQ ID NOs:12, 14, and 16.

In an eighth embodiment, the invention relates to a method of selecting an isolated polynucleotide that affects the level of expression of a CTP:phosphoethanolamine cytidylyltransferase or a phosphatidylethanolamine N-methyltransferase polypeptide or enzyme activity in a host cell, preferably a plant cell, the method comprising the steps of: (a) constructing an isolated polynucleotide of the present invention or an isolated chimeric gene of the present invention; (b) introducing the isolated polynucleotide or the isolated chimeric gene into a host cell; (c) measuring the level of the CTP:phosphoethanolamine cytidylyltransferase or the phosphatidylethanolamine N-methyltransferase polypeptide or enzyme activity in the host cell containing the isolated polynucleotide; and (d) comparing the level of the CTP:phosphoethanolamine cytidylyltransferase or the phosphatidylethanolamine N-methyltransferase polypeptide or enzyme activity in the host cell containing the isolated polynucleotide with the level of the CTP:phosphoethanolamine cytidylyltransferase or the phosphatidylethanolamine N-methyltransferase polypeptide or enzyme activity in the host cell that does not contain the isolated polynucleotide.

In a ninth embodiment, the invention concerns a method of obtaining a nucleic acid fragment encoding a substantial portion of a CTP:phosphoethanolamine cytidylyltransferase or a phosphatidylethanolamine N-methyltransferase, preferably a plant CTP:phosphoethanolamine cytidylyltransferase or phosphatidylethanolamine N-methyltransferase, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, and 19, and the complement of such nucleotide sequences; and amplifying a nucleic acid fragment (preferably a cDNA inserted in a cloning vector) using the oligonucleotide primer. The amplified nucleic acid fragment preferably will encode a substantial portion of a CTP:phosphoethanolamine cytidylyltransferase or a phosphatidylethanolamine N-methyltransferase amino acid sequence.

In a tenth embodiment, this invention relates to a method of obtaining a nucleic acid fragment encoding all or a substantial portion of the amino acid sequence encoding a CTP:phosphoethanolamine cytidylyltransferase or a phosphatidylethanolamine N-methyltransferase polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

In an eleventh embodiment, this invention concerns a composition, such as a hybridization mixture, comprising an isolated polynucleotide of the present invention.

In a twelfth embodiment, this invention concerns a method for positive selection of a transformed cell comprising: (a) transforming a host cell with the chimeric gene of the present invention or an expression cassette of the present invention; and (b) growing the transformed host cell, preferably a plant cell, such as a monocot or a dicot, under conditions which allow expression of the phosphatidylcholine biosynthetic enzyme in an amount sufficient to complement an auxotroph to provide a positive selection means.

In a thirteenth embodiment, this invention relates to a method of altering the level of expression of a phosphatidylcholine biosynthetic enzyme in a host cell comprising: (a) transforming a host cell with a chimeric gene of the present invention; and (b) growing the transformed host cell under conditions that are suitable for expression of the chimeric gene wherein expression of the chimeric gene results in production of altered levels of the phosphatidylcholine biosynthetic enzyme in the transformed host cell.

A further embodiment of the instant invention is a method for evaluating at least one compound for its ability to inhibit the activity of a phosphatidylcholine biosynthetic enzyme, the method comprising the steps of: (a) transforming a host cell with a chimeric gene comprising a nucleic acid fragment encoding a phosphatidylcholine biosynthetic enzyme polypeptide, operably linked to suitable regulatory sequences; (b) growing the transformed host cell under conditions that are suitable for expression of the chimeric gene wherein expression of the chimeric gene results in production of phosphatidylcholine biosynthetic enzyme in the transformed host cell; (c) optionally purifying the phosphatidylcholine biosynthetic enzyme expressed by the transformed host cell; (d) treating the phosphatidylcholine biosynthetic enzyme with a compound to be tested; and (e) comparing the activity of the phosphatidylcholine biosynthetic enzyme that has been treated with a test compound to the activity of an untreated phosphatidylcholine biosynthetic enzyme, and selecting compounds with potential for inhibitory activity.

BRIEF DESCRIPTION OF THE SEQUENCE LISTINGS

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Phosphatidylcholine Biosynthetic Enzymes

| | | SEQ ID NO: | |
|---|---|---|---|
| Protein | Clone Designation | (Nucleotide) | (Amino Acid) |
| Corn phosphoethanolamine cytidylyltransferase | cc71se-b.pk0008.g2 | 1 | 2 |
| Rice phosphoethanolamine cytidylyltransferase | rls48.pk0009.h11 | 3 | 4 |
| Soybean phosphoethanolamine cytidylyltransferase | sr1.pk0136.h8 | 5 | 6 |
| Wheat phosphoethanolamine cytidylyltransferase | wle1n.pk0092.b3 | 7 | 8 |

TABLE 1-continued

Phosphatidylcholine Biosynthetic Enzymes

| Protein | Clone Designation | SEQ ID NO: (Nucleotide) | SEQ ID NO: (Amino Acid) |
|---|---|---|---|
| Wheat phosphatidylethanolamine N-methyltransferase | wlm96.pk028.h24 | 9 | 10 |
| Corn phosphoethanolamine cytidylyltransferase | Contig of: p0121.cfrmp55r:fis p0121.cfrmz88r | 11 | 12 |
| Rice phosphoethanolamine cytidylyltransferase | rls48.pk0009.h11:fis | 13 | 14 |
| Soybean phosphoethanolamine cytidylyltransferase | sr1.pk0136.h8:fis | 15 | 16 |
| Wheat phosphoethanolamine cytidylyltransferase | wle1n.pk0092.b3:fis | 17 | 18 |
| Wheat phosphatidylethanolamine N-methyltransferase | wlm96.pk028.h24:fis | 19 | 20 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least one of 60 contiguous nucleotides, preferably at least one of 40 contiguous nucleotides, most preferably one of at least 30 contiguous nucleotides derived from SEQ ID NOs:1, 3, 5, 7, 9, 11, 13, 15, 17, and 19, or the complement of such sequences.

The term "isolated" polynucleotide refers to a polynucleotide that is substantially free from other nucleic acid sequences, such as and not limited to other chromosomal and extrachromosomal DNA and RNA. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can.then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, and 19, and the complement of such nucleotide sequences may be used in methods of selecting an isolated polynucleotide that affects the expression of a CTP:phosphoethanolamine cytidylyltransferase or a phosphatidylethanolamine N-methyltransferase in a host cell. A method of selecting an isolated polynucleotide that affects the level of expression of a polypeptide in a virus or in a host cell (eukaryotic, such as plant or yeast, prokaryotic such as bacterial) may comprise the steps of: constructing an isolated polynucleotide of the present invention or an isolated chimeric gene of the present invention; introducing the isolated polynucleotide or the isolated chimeric gene into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above identities but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Condon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign-gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

"3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Auxotroph" refers here to an organism that requires a specific growth factor (an amino acid, for example) for its growth.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100: 1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature (London)* 327:70–73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

"PCR" or "polymerase chain reaction" is well known by those skilled in the art as a technique used for the amplification of specific DNA segments (U.S. Pat. Nos. 4,683,195 and 4,800,159).

The present invention concerns an isolated polynucleotide comprising a nucleotide sequence selected from the group consisting of: (a) a first nucleotide sequence encoding a polypeptide of at least 40 amino acids having at least 80% identity based on the Clustal method of alignment when compared to a polypeptide selected from the group consisting of SEQ ID NOs:2, 4, 6, 8, 10, 18, and 20, (b) a second nucleotide sequence encoding a polypeptide of at least 200 amino acids having at least 80% identity based on the Clustal method of alignment when compared to a polypeptide selected from the group consisting of SEQ ID NOs:12, 14, and 18, and (c) a third nucleotide sequence comprising the complement of the first or second nucleotide sequences.

In a second embodiment, it is preferred that the isolated polynucleotide of the claimed invention comprises nucleotide sequence selected from: (a) a first nucleotide sequence of at least 100 nucleotides having at least 80% identity based on the Clustal method of alignment when compared to a nucleotide sequence selected from SEQ ID NOs:1, 3, 5, 7, 9, 17, and 19, and (b) a second nucleotide sequence selected from the group consisting of SEQ ID NOs:11, 13, and 15.

Nucleic acid fragments encoding at least a portion of several phosphatidylcholine biosynthetic enzymes have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other phosphoethanolamine cytidylyltransferases or phosphatidylethanolamine N-methyltransferases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 60 (preferably one of at least 40, most preferably one of at least 30) contiguous nucleotides derived from a nucleotide sequence selected from the group consisting of SEQ ID NOs:1, 3, 5, 7, 9, 11, 13, 15, 17, and 19 and the complement of such nucleotide sequences may be used in such methods to obtain a nucleic acid fragment encoding a substantial portion of an amino acid sequence of a polypeptide.

The present invention relates to a method of obtaining a nucleic acid fragment encoding a substantial portion of a CTP:phosphoethanolamine cytidylyltransferase or a phosphatidylethanolamine N-methyltransferase polypeptide, preferably a substantial portion of a plant CTP:phosphoethanolamine cytidylyltransferase or phosphatidylethanolamine N-methyltransferase, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, and 19, and the complement of such nucleotide sequences; and amplifying a nucleic acid fragment (preferably a cDNA inserted in a cloning vector) using the oligonucleotide primer. The amplified nucleic acid fragment preferably will encode a portion of a CTP:phosphoethanolamine cytidylyltransferase or a phosphatidylethanolamine N-methyltransferase polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

In another embodiment, this invention concerns viruses and host cells comprising either the chimeric genes of the invention as described herein or an isolated polynucleotide of the invention as described herein. Examples of host cells which can be used to practice the invention include, but are not limited to, yeast, bacteria, and plants.

The nucleic acid fragments of the instant invention may be used to create transgenic plants in which the disclosed polypeptides are present at higher or lower levels than normal or in cell types or developmental stages in which they are not normally found. This would have the effect of altering the ratio of phosphoethanolamine/ phosphotidylcholine (PE/PC) in those cells. PC is a trimethylated form of PE; overexpression of phosphatidylethanolamine N-methyltransferase will lead to more PC from PE. It might be necessary to increase PE production for this to work well. Phosphoethanolamine cytidylyltransferase controls the synthesis of PE so its overexpression should yield higher levels of PE. Lecithin is extracted from soy oil during processing and is a mix of PE and PC. It is used as an emulsifier in chocolate (to replace cocoa butter) and as a nutritional supplement. Soybean lecithin is fractionated to obtain a higher content of PC to be sold as a nutritional supplement. Increasing the PC content of soybean lecithin from its normal 14% to 35% will improve its value as nutritional supplement. Increasing the PC content of soybean to 25% will improve its emulsifying qualities and it would be possible to replace cocoa butter in chocolate, thereby increasing its commercial value.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention concerns a polypeptide of at least 40 amino acids that has at least 80% identity based on the Clustal method of alignment when compared to a polypeptide selected from SEQ ID NOs:2, 4, 6, 8, 10, 18, or 20; or a polypeptide of at least 200 amino acids that has at least 80% identity based on the Clustal method of alignment when compared to a polypeptide selected from the group consisting of SEQ ID NOs:12, 14, and 16.

The instant polypeptides (or portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded phosphatidylcholine biosynthetic enzyme. An example of a vector for high level expression of the instant polypeptides in a bacterial host is provided (Example 7).

Additionally, the instant polypeptides can be used as a target to facilitate design and/or identification of inhibitors of those enzymes that may be useful as herbicides. This is desirable because the polypeptides described herein catalyze various steps in phosphatidylcholine biosynthethesis. Accordingly, inhibition of the activity of one or more of the enzymes described herein could lead to inhibition of plant growth. Thus, the instant polypeptides could be appropriate for new herbicide discovery arid design.

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth in here is incorporated herein by reference in its entirety.

Example 1

Composition of cDNA Libraries, Isolation and Sequencing of cDNA Clones cDNA libraries representing mRNAs from various corn, rice, soybean, and wheat tissues were prepared. The characteristics of the libraries are described below.

TABLE 2 cDNA Libraries from Corn, Rice, Soybean, and Wheat

| Library | Tissue | Clone |
| --- | --- | --- |
| cc71se-b | Corn Callus Type II Tissue, Somatic Embryo Formed | cc71se-b.pk0008.g2 |
| p0121 | Corn Shank Ear Tissue Collected 5 Days After Pollination* | p0121.cfrmp55r |
| p0121 | Corn Shank Ear Tissue Collected 5 Days After Pollination* | p0121.cfrmz88r |
| rls48 | Rice Leaf 15 Days After Germination, 48 Hours After Infection of Strain *Magaporthe grisea* 4360-R-67 (AVR2-YAMO); Susceptible | rls48.pk0009.h11 |
| sr1 | Soybean Root | sr1.pk0136.h8 |
| wle1n | Wheat Leaf From 7 Day Old Etiolated Seedling* | wle1n.pk0092.b3 |
| wlm96 | Wheat Seedlings 96 Hours After Inoculation With *Erysiphe graminis* f. sp *tritici* | wlm96.pk028.h24 |

*These libraries were normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765–3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147–5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred/Phrap (P. Green, University of Washington, Seattle). Phrep/Phrap is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (D. Gordon, University of Washington, Seattle).

Example 2

Identification of cDNA Clones cDNA clones encoding phosphatidylcholine biosynthetic enzymes were identified by conducting BLAST (Basic Local Alignment Search Tool; Altschul et al. (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the, pLog value, the greater the likelihood that the cDNA sequence and the BLAST "hit" represent homologous proteins.

ESTs submitted for analysis are compared to the genbank database as described above. ESTs that contain sequences more 5- or 3-prime can be found by using the BLASTn algorithm (Altschul et al (1997) *Nucleic Acids Res.* 25:3389–3402.) against the Du Pont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described in Example 1. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 3

Characterization of cDNA Clones Encoding CTP Phosphoethanolamine Cytidylyltransferase The BLASTX search using the EST sequences from clones listed in Table 3 revealed similarity of the polypeptides encoded by the contig to a putative phosphoethanolamine cytidylyltransferase from *Arabidopsis thaliana* (NCBI General Identifier No. 3786005) and by the cDNAs to CTP phosphoethanolamine cytidylyltransferase from *Homo sapiens* and *Rattus norvegicus* (NCBI General Identifier Nos. 4505651 and 3396102, respectively). Shown in Table 3 are the BLAST results for individual ESTs and the NCBI General Identifier Nos. of the two sequences with closest homology:

TABLE 3

BLAST Results for Sequences Encoding Polypeptides Homologous to Phosphoethanolamine Cytidylyltransferase

| Clone | NCBI General Identifier No. | BLAST pLog Score |
|---|---|---|
| cc71se-b.pk0008.g2 | 4505651 | 33.00 |
| | 3786005 | 76.70 |
| rls48.pk0009.h11 | 4505651 | 17.00 |
| | 3786005 | 34.30 |
| sr1.pk0136.h8 | 4505651 | 25.15 |
| | 3786005 | 50.70 |
| wle1n.pk0092.b3 | 3396102 | 8.30 |
| | 3786005 | 26.52 |

The sequence of the entire cDNA insert in clone cc71se-b.pk0008.g2 could not be obtained, thus a corn contig was identified that covers most of the same region at the 5' end and is longer at the 3' terminus. The sequence of the entire cDNA insert in the remaining clones listed in Table 3 was determined. The sequences towards the 5' terminus from the rice and soybean sequences were obtained using PCR techniques well known to those skilled in the art.

The BLASTX search using the EST sequences from clones listed in Table 4 revealed similarity of the polypeptides encoded by the Contigs to putative phospholipid cytidylyltransferase from *Arabidopsis thaliana* (NCBI General Identifier No. 3786005) and CG5547 gene product [alt 2] from *Drosophila melanogaster* (NCBI General Identifier No. 7298016), and by the cDNAs to CTP:phosphoethanolamine cytidylyltransferase from *Homo sapiens* and *Rattus norvegicus* (NCBI General Identifier Nos. 4505651 and 3396102, respectively). Shown in Table 4 are the BLAST results for the sequences of the entire cDNA inserts comprising the indicated cDNA clones ("FIS"), the sequences of contigs assembled from two or more ESTs ("Contig"), or sequences assembled from FIS and 5' PCR encoding the entire protein ("CGS"):

TABLE 4

BLAST Results for Sequences Encoding Polypeptides Homologous to CTP:Phosphoethanolamine Cytidylyltransferase

| Clone | Status | BLAST pLog Score | | | |
|---|---|---|---|---|---|
| | | 3786005 | 7298016 | 4505651 | 3396102 |
| Contig of: p0121.cfrmp55r:fis p0121.cfrmz88r | Contig | 97.52 | 62.00 | 57.22 | 56.40 |
| rls48.pk0009.h11:fis | CGS | >180.00 | 85.52 | 90.70 | 87.40 |
| sr1.pk0136.h8:fis | CGS | 173.00 | 78.52 | 80.10 | 78.52 |
| wle1n.pk0092.b3:fis | FIS | 24.52 | 4.15 | 7.00 | 18.52 |

The data in Table 5 presents a calculation of the percent identity of the amino acid sequences set forth in SEQ ID NOs:2, 4, 6, 8, 12, 14, 16, and 18 and the *Arabidopsis thaliana* and *Homo sapiens* sequences ((NCBI General Identifier Nos. 3786005 and 4505651).

TABLE 5

Percent Identity of Amino Acid Sequences Deduced From the Nucleotide Sequences of cDNA Clones Encoding Polypeptides Homologous to CTP:Phosphoethanolamine Cytidylyltransferase

| SEQ ID NO. | Percent Identity to | |
|---|---|---|
| | 3786005 | 4505651 |
| 2 | 79.6 | 40.8 |
| 4 | 71.1 | 33.7 |
| 6 | 89.8 | 50.9 |
| 8 | 77.2 | 40.4 |
| 12 | 69.4 | 36.2 |
| 14 | 73.4 | 39.6 |
| 16 | 58.7 | 37.5 |
| 18 | 70.8 | 31.9 |

Nucleotides 846 through 1409 from corn clone having SEQ ID NO:11 are 96% identical to nucleotides 563 through 1 from corn EST having NCBI General Identifier No. 6012413. Nucleotides 1372 through 1827 from rice clone having SEQ ID NO:13 are 96% identical to nucleotides 1 through 443 from rice EST having NCBI General Identifier No. 3760654. Nucleotides 1422 through 1840 from soybean clone having SEQ ID NO:15 are 99% identical to nucleotides 1 through 519 from soybean EST having NCBI General Identifier No. 85973.

Sequence alignments and percent identity calculations were performed using the Megalign program of the LASERGENE bioinformatics computing suite (DNASTAR Inc., Madison, Wis. Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of two corn CTP:phosphoethanolamine cytidylyltransferase variants, a substantial portion and the entire rice and soybean CTP:phosphoethanolamine cytidylyltransferases and substantial portions of one wheat CTP:phosphoethanolamine cytidylyltransferase. These sequences represent the first corn, rice, soybean, and wheat sequences encoding CTP:phosphoethanolamine cytidylyltransferase known to Applicant.

Example 4

Characterization of cDNA Clones Encoding Phosphatidylethanolamine N-Methyltransferase The BLASTX search using the EST sequences from clone listed in Table 6 revealed similarity of the polypeptides encoded by the cDNAs to phosphatidylethanolamine N-methyltransferase from Homo sapiens (NCBI General Identifier No. 5459516). Shown in Table 6 are the BLAST results for individual EST:

TABLE 6

BLAST Results for Sequences Encoding Polypeptides Homologous to Phosphatidylethanolamine N-Methyltransferase

| Clone | Status | BLAST pLog Score 5459516 |
|---|---|---|
| wlm96.pk028.h24 | EST | 34.9 |

The sequence of the entire cDNA insert in clone listed in Table 6 was determined. The BLASTX search using the EST sequences from clone listed in Table 7 revealed similarity of the polypeptides encoded by the cDNAs to phosphatidylethanolamine N-methyltransferase from *Saccharomyces cerevisiae* (NCBI General Identifier No. 6322533). Shown in Table 7 are the BLAST results for the sequences of the entire cDNA insert comprising the indicated cDNA clone encoding the entire protein ("CGS"):

TABLE 7

BLAST Results for Sequences Encoding Polypeptides
Homologous to Phosphatidylethanolamine N-Methyltransferase

| Clone | Status | BLAST pLog Score 6322533 |
|---|---|---|
| wlm96.pk028.h4:fis | CGS | 58.22 |

The data in Table 8 presents a calculation of the percent identity of the amino acid sequences set forth in SEQ ID NOs:10 and 20 and the *Saccharomyces cerevisiae* sequence (NCBI General Identifier No. 6322533).

TABLE 8

Percent Identity of Amino Acid Sequences Deduced From the Nucleotide Sequences of cDNA Clones Encoding Polypeptides Homologous to Phosphatidylethanolamine N-Methyltransferase

| SEQ ID NO. | Percent Identity to 6322533 |
|---|---|
| 10 | 53.5 |
| 20 | 54.4 |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion and an entire wheat phosphatidylethanolamine N-methyltransferase. These sequences represent the first plant sequences encoding phosphatidylethanolamine N-methyltransferase known to Applicant.

Example 5

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110–2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega; Madison, Wis.). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 m in diameter) are coated with DNA using the following technique. Ten µg of plasmid DNAs are added to 50 µL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 6

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µl spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 µg/ml ethidium bromide for visualization of the DNA fragment. The fragment can then be purified from the agarose gel by digestion with GELase™ (Epicentre Technologies, Madison, Wis.) according to the manufacturer's instructions, ethanol precipitated, dried and resuspended in 20 μL of water. Appropriate oligonucleotide adapters may be ligated to the fragment using T4 DNA ligase (New England Biolabs (NEB), Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21 (DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 8

Evaluating Compounds for Their Ability to Inhibit the Activity of Phosphatidylcholine Biosynthetic Enzymes The polypeptides described herein may be produced using any number of methods known to those skilled in the art. Such methods include, but are not limited to, expression in bacteria as described in Example 6, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. For example, assays for phosphoethanolamine cytidylyltransferase are presented by Sundler (1975) *J. Biol. Chem.* 250:8585–8590. Assays for phosphatidylethanolamine N-methyltransferase are presented by Vance and Schneider (1981) *Methods Enzymol.* 71:581–588.

---

What is claimed is:

1. An isolated polynucleotide comprising:
   (a) a nucleotide sequence encoding a polypeptide having phosphatidylethanolamine N-methyltransferase activity, wherein the amino acid sequence of the polypeptide and the amino acid sequence of SEQ ID NO:20 have at least 80% sequence identity based on the Clustal alignment method, or
   (b) the complement of the nucleotide sequence, wherein the complement and the nucleotide sequence contain the same number of nucleotides and are 100% complementary.

2. The polynucleotide of claim 1 wherein the amino acid sequence of the polypeptide and the amino acid sequence of SEQ ID NO:20 have at least 85% sequence identity based on the Clustal alignment method.

3. The polynucleotide of claim 1 wherein the amino acid sequence of the polypeptide and the amino acid sequence of SEQ ID NO:20 have at least 90% sequence identity based on the Clustal alignment method.

4. The polynucleotide of claim 1 wherein the amino acid sequence of the polypeptide and the amino acid sequence of SEQ ID NO:20 have at least 95% sequence identity based on the Clustal alignment method.

5. The polynucleotide of claim 1 wherein the polypeptide comprises the amino acid sequence of SEQ ID NO:20.

6. The polynucleotide of claim 1 wherein the nucleotide sequence comprises the nucleotide sequence of SEQ ID NO:19.

7. A vector comprising the polynucleotide of claim 1.

8. A recombinant DNA construct comprising the polynucleotide of claim 1 operably linked to a regulatory sequence.

9. A method for transforming a cell comprising transforming a cell with the polynucleotide of claim 1.

10. A cell comprising the recombinant DNA construct of claim 8.

11. A method for producing a plant comprising transforming a plant cell with the polynucleotide of claim 1 and regenerating a plant from the transformed plant cell.

12. A plant comprising the recombinant DNA construct of claim 8.

13. A seed comprising the recombinant DNA construct of claim 8.

* * * * *

UNITED STATES PATENT AND TRADEMARK OFFICE
CERTIFICATE OF CORRECTION

PATENT NO. : 6,596,926 B1
DATED : July 22, 2003
INVENTOR(S) : Famodu Omolayo O. and Kinney Anthony It is certified that error appears in the above-identified patent and that said Letters Patent is hereby corrected as shown below:

Title page,
Item [75], Inventors, please delete "J. Antoni Rafalski, Wilmington, DE (US)".

Signed and Sealed this

Eighteenth Day of May, 2004

JON W. DUDAS
*Acting Director of the United States Patent and Trademark Office*

SEQUENCE LISTING

<160> NUMBER OF SEQ ID NOS: 20

<210> SEQ ID NO 1
<211> LENGTH: 530
<212> TYPE: DNA
<213> ORGANISM: Zea mays

<400> SEQUENCE: 1

```
cagcgacgac gagatcaagg ccaacaaggg accccccgtc acgccgctcc acgagagaat      60
ggtaatggtc cgtgctgtga aatgggtgga tgatatcatt ccagatgcac cttatgccat     120
```

-continued

```
aactgaagaa ttcatgaaca aactattcaa tgagtacaac atagactaca ttatccatgg      180
agacgatcct tgtttgctac ctgatggtac tgatgcctat gctcttgcca aaaaggctgg      240
tcgatacaag cagattaaga gaaccgaggg agtgtcgaca acagacattg ttggacggat      300
gcttctttgt gttagagaga gatcatctga tgcacataac cactcgtcac tacaaaggca      360
gttcagtagt ggacatggtc agaaagttga tgatactgga tctggaactg aacaagagt      420 atctcatttt cttcccacat ctaggcgaat agttcaattc tcaaatagca agggtcaggt      480
ccagattctc ggatagttta catagatggt gcttttgatc tgttccatgc                 530
```

<210> SEQ ID NO 2
<211> LENGTH: 157
<212> TYPE: PRT
<213> ORGANISM: Zea mays

<400> SEQUENCE: 2

```
Ser Asp Asp Glu Ile Lys Ala Asn Lys Gly Pro Pro Val Thr Pro Leu
 1               5                  10                  15

His Glu Arg Met Val Met Val Arg Ala Val Lys Trp Val Asp Asp Ile
            20                  25                  30

Ile Pro Asp Ala Pro Tyr Ala Ile Thr Glu Glu Phe Met Asn Lys Leu
        35                  40                  45

Phe Asn Glu Tyr Asn Ile Asp Tyr Ile Ile His Gly Asp Asp Pro Cys
    50                  55                  60

Leu Leu Pro Asp Gly Thr Asp Ala Tyr Ala Leu Ala Lys Lys Ala Gly
65                  70                  75                  80

Arg Tyr Lys Gln Ile Lys Arg Thr Glu Gly Val Ser Thr Thr Asp Ile
                85                  90                  95

Val Gly Arg Met Leu Leu Cys Val Arg Glu Arg Ser Ser Asp Ala His
            100                 105                 110

Asn His Ser Ser Leu Gln Arg Gln Phe Ser Ser Gly His Gly Gln Lys
        115                 120                 125

Val Asp Asp Thr Gly Ser Gly Thr Gly Thr Arg Val Ser His Phe Leu
    130                 135                 140

Pro Thr Ser Arg Arg Ile Val Gln Phe Ser Asn Ser Lys
145                 150                 155
```

<210> SEQ ID NO 3
<211> LENGTH: 544
<212> TYPE: DNA
<213> ORGANISM: Oryza sativa
<220> FEATURE:
<221> NAME/KEY: unsure
<222> LOCATION: (205)
<223> OTHER INFORMATION: n = A, C, G or T
<220> FEATURE:
<221> NAME/KEY: unsure
<222> LOCATION: (269)
<223> OTHER INFORMATION: n = A, C, G or T
<220> FEATURE:
<221> NAME/KEY: unsure
<222> LOCATION: (354)
<223> OTHER INFORMATION: n = A, C, G or T
<220> FEATURE:
<221> NAME/KEY: unsure
<222> LOCATION: (436)
<223> OTHER INFORMATION: n = A, C, G or T
<220> FEATURE:
<221> NAME/KEY: unsure
<222> LOCATION: (438)
<223> OTHER INFORMATION: n = A, C, G or T
<220> FEATURE:

```
<221> NAME/KEY: unsure
<222> LOCATION: (455)
<223> OTHER INFORMATION: n = A, C, G or T
<220> FEATURE:
<221> NAME/KEY: unsure
<222> LOCATION: (462)
<223> OTHER INFORMATION: n = A, C, G or T
<220> FEATURE:
<221> NAME/KEY: unsure
<222> LOCATION: (474)..(475)
<223> OTHER INFORMATION: n = A, C, G or T
<220> FEATURE:
<221> NAME/KEY: unsure
<222> LOCATION: (481)
<223> OTHER INFORMATION: n = A, C, G or T
<220> FEATURE:
<221> NAME/KEY: unsure
<222> LOCATION: (490)..(491)
<223> OTHER INFORMATION: n = A, C, G or T
<220> FEATURE:
<221> NAME/KEY: unsure
<222> LOCATION: (525)
<223> OTHER INFORMATION: n = A, C, G or T
<220> FEATURE:
<221> NAME/KEY: unsure
<222> LOCATION: (532)
<223> OTHER INFORMATION: n = A, C, G or T

<400> SEQUENCE: 3
tgtatcgtta gagagagatc agcttctgat agtcacaacc actcttcact acaaaggcag      60
ttcagtcacg ggcatggcca gaaaattgat gatagtggat ctggaagtgg aactaggata     120
tctcattttc ttcctacatc tcggagaata gttcagttct caaatagcag ggtccaggt     180 ccagattctc ggatagtgta catanatggt gcatttgatc tattccatgc tggacatgtt     240
gagatattgc gcctcgctcg agagcttgng agatttcctg cttgtgggta ttcacacaag     300
accagactat aagttcaaca gaggaccac atcgcccaat catgaacctc catnagagaa     360
gtttgagtgt tttggcttgc cgttatgttg atgaatgatc atggggctcc atgggatgtt     420
tccgaaagat atgatnanca catttaataa ttccnttggg tnttcatggg acanntgctg     480
ngaatatggn nttatgaagg atgattaatc catatgctgt tcaangggta tnggcatcta     540
ccgt                                                                  544

<210> SEQ ID NO 4
<211> LENGTH: 83
<212> TYPE: PRT
<213> ORGANISM: Oryza sativa
<220> FEATURE:
<221> NAME/KEY: UNSURE
<222> LOCATION: (59)
<223> OTHER INFORMATION: Xaa = any amino acid
<220> FEATURE:
<221> NAME/KEY: UNSURE
<222> LOCATION: (80)
<223> OTHER INFORMATION: Xaa = any amino acid

<400> SEQUENCE: 4

Ser His Asn His Ser Ser Leu Gln Arg Gln Phe Ser His Gly His Gly
  1               5                  10                  15

Gln Lys Ile Asp Asp Ser Gly Ser Gly Ser Gly Thr Arg Ile Ser His
             20                  25                  30

Phe Leu Pro Thr Ser Arg Arg Ile Val Gln Phe Ser Asn Ser Arg Gly
         35                  40                  45

Pro Gly Pro Asp Ser Arg Ile Val Tyr Ile Xaa Gly Ala Phe Asp Leu
     50                  55                  60
```

Phe His Ala Gly His Val Glu Ile Leu Arg Leu Ala Arg Glu Leu Xaa
  65                  70                  75                  80

Arg Phe Pro
        83

<210> SEQ ID NO 5
<211> LENGTH: 471
<212> TYPE: DNA
<213> ORGANISM: Glycine max
<220> FEATURE:
<221> NAME/KEY: unsure
<222> LOCATION: (18)
<223> OTHER INFORMATION: n = A, C, G or T
<220> FEATURE:
<221> NAME/KEY: unsure
<222> LOCATION: (135)..(136)
<223> OTHER INFORMATION: n = A, C, G or T
<220> FEATURE:
<221> NAME/KEY: unsure
<222> LOCATION: (402)
<223> OTHER INFORMATION: n = A, C, G or T
<220> FEATURE:
<221> NAME/KEY: unsure
<222> LOCATION: (408)
<223> OTHER INFORMATION: n = A, C, G or T
<220> FEATURE:
<221> NAME/KEY: unsure
<222> LOCATION: (447)
<223> OTHER INFORMATION: n = A, C, G or T
<220> FEATURE:
<221> NAME/KEY: unsure
<222> LOCATION: (461)
<223> OTHER INFORMATION: n = A, C, G or T
<220> FEATURE:
<221> NAME/KEY: unsure
<222> LOCATION: (467)
<223> OTHER INFORMATION: n = A, C, G or T
<220> FEATURE:
<221> NAME/KEY: unsure
<222> LOCATION: (471)
<223> OTHER INFORMATION: n = A, C, G or T

<400> SEQUENCE: 5
cttcgccaag ctcgtgcnct cggcgaccag ttgattgttg gggttgttag tgatgcagag     60
atcattgcca ataagggccc ccccgttacc cctcttcacg aaaggttgat aatggtgaat    120
gcggtgaagt gggtnnatga ggttattcct gaagctccct atgcgataac cgaggagttc    180
atgaagaagc tttttgatga gtacaagata gattacatta ttcacgggga tgatccttgt    240
gttcttccgg atggaactga tgcttatgct catgctaaga aggctggtcg atataagcag    300
ataaagcgta ctgaaggggt ttcacactga tattgttggt cgatcttctc tgtgtaaaga    360
aggtctatta ctgaaaaatc ataatcattc ttctttacaa ancatcanca atggcatagt    420
cgagttgagc tgtcactgct gcactgnagt gactcgtata ntctttntgc n             471

<210> SEQ ID NO 6
<211> LENGTH: 108
<212> TYPE: PRT
<213> ORGANISM: Glycine max
<220> FEATURE:
<221> NAME/KEY: UNSURE
<222> LOCATION: (46)
<223> OTHER INFORMATION: Xaa = any amino acid

<400> SEQUENCE: 6

Leu Arg Gln Ala Arg Ala Leu Gly Asp Gln Leu Ile Val Gly Val Val
  1               5                  10                  15

Ser Asp Ala Glu Ile Ile Ala Asn Lys Gly Pro Pro Val Thr Pro Leu
            20                  25                  30

His Glu Arg Leu Ile Met Val Asn Ala Val Lys Trp Val Xaa Glu Val
        35                  40                  45

Ile Pro Glu Ala Pro Tyr Ala Ile Thr Glu Glu Phe Met Lys Lys Leu
    50                  55                  60

Phe Asp Glu Tyr Lys Ile Asp Tyr Ile Ile His Gly Asp Asp Pro Cys
65                  70                  75                  80

Val Leu Pro Asp Gly Thr Asp Ala Tyr Ala His Ala Lys Lys Ala Gly
                85                  90                  95

Arg Tyr Lys Gln Ile Lys Arg Thr Glu Gly Val Ser
            100                 105

<210> SEQ ID NO 7
<211> LENGTH: 493
<212> TYPE: DNA
<213> ORGANISM: Triticum aestivum
<220> FEATURE:
<221> NAME/KEY: unsure
<222> LOCATION: (398)..(399)
<223> OTHER INFORMATION: n = A, C, G or T
<220> FEATURE:
<221> NAME/KEY: unsure
<222> LOCATION: (459)
<223> OTHER INFORMATION: n = A, C, G or T
<220> FEATURE:
<221> NAME/KEY: unsure
<222> LOCATION: (462)
<223> OTHER INFORMATION: n = A, C, G or T
<220> FEATURE:
<221> NAME/KEY: unsure
<222> LOCATION: (468)
<223> OTHER INFORMATION: n = A, C, G or T
<220> FEATURE:
<221> NAME/KEY: unsure
<222> LOCATION: (475)
<223> OTHER INFORMATION: n = A, C, G or T
<220> FEATURE:
<221> NAME/KEY: unsure
<222> LOCATION: (484)
<223> OTHER INFORMATION: n = A, C, G or T

<400> SEQUENCE: 7
aacatggact atacagagga tgattcaaat ccatatgctg ctccaattgc tatgggcatt     60
tatcataagc tggatagccc tttggacatc accactagta ctattataag gagaatagtt    120
tctaaccatg aagcctacca gaaacggaat gagaagaagg aagccagcga gaagaagtac    180
tatgacagta aaagtttgtc aatgggagag taagtgactt ctgaatagtt ctcctcaaga    240
agactgttcc tgggttcttt tggaggctct aacacaggtc acaaatggaa accatcaagt    300
ggatcctcca attttaccgc tccattgtca tttttggcta tatacttaat gcttcaagat    360
gcatccttga tgcatgacag catgctgctg aattgggnnc cggacctgga tgatttccaa    420
tgggcacttc aatgccacta ctacctaccc ccccggtana cnggttcnaa acgcnttacg    480
gccnatcttt tgg                                                      493

<210> SEQ ID NO 8
<211> LENGTH: 57
<212> TYPE: PRT
<213> ORGANISM: Triticum aestivum

<400> SEQUENCE: 8

Asp Asp Ser Asn Pro Tyr Ala Ala Pro Ile Ala Met Gly Ile Tyr His
1               5                   10                  15

Lys Leu Asp Ser Pro Leu Asp Ile Thr Thr Ser Thr Ile Ile Arg Arg
            20                  25                  30

Ile Val Ser Asn His Glu Ala Tyr Gln Lys Arg Asn Glu Lys Lys Glu
        35                  40                  45

Ala Ser Glu Lys Lys Tyr Tyr Asp Ser
    50                  55

<210> SEQ ID NO 9
<211> LENGTH: 525
<212> TYPE: DNA
<213> ORGANISM: Triticum aestivum
<220> FEATURE:
<221> NAME/KEY: unsure
<222> LOCATION: (485)
<223> OTHER INFORMATION: n = A, C, G or T

<400> SEQUENCE: 9
tgaaaattgg cgttgttaag gtcaagtctg gcattatgga aggtccatct acaaatttga      60
tcgaatttat cgacttgagt cagaaaagtt ttgccattgc ggctggatcg attttgttta    120
acccaacatt ctggaatatc gttgcgcgaa aagaatatca tgataagtcc ctaactaaac    180
ttgctggtgg caatgcacgc tcggctgtt atatactcgc agttaccatc ttttgcttgg     240
ggatattccg agattttctc tatgagcgcg ccctccgtga tcagcctacc atgccactct    300
tgttgacaac cccctttcag cttctaagcc cttgttttag ttatttcagg caatatccta    360
gtcatatcct caatgtgggc cctcggaata actggtacat accttggtga ttatttcgga    420
attctaatgg acgaaatggt gacgggcttc ccgtttaatg ttaccgacgc accatgtatt    480
acggnagcac aatgagtttc ccaaggacag cactaatcct tggaa                    525

<210> SEQ ID NO 10
<211> LENGTH: 86
<212> TYPE: PRT
<213> ORGANISM: Triticum aestivum

<400> SEQUENCE: 10

Thr Asn Leu Ile Glu Phe Ile Asp Leu Ser Gln Lys Ser Phe Ala Ile
1               5                   10                  15

Ala Ala Gly Ser Ile Leu Phe Asn Pro Thr Phe Trp Asn Ile Val Ala
            20                  25                  30

Arg Lys Glu Tyr His Asp Lys Ser Leu Thr Lys Leu Ala Gly Gly Asn
        35                  40                  45

Ala Arg Leu Gly Cys Tyr Ile Leu Ala Val Thr Ile Phe Cys Leu Gly
    50                  55                  60

Ile Phe Arg Asp Phe Leu Tyr Glu Arg Ala Leu Arg Asp Gln Pro Thr
65                  70                  75                  80

Met Pro Leu Leu Leu Thr
                85

<210> SEQ ID NO 11
<211> LENGTH: 1436
<212> TYPE: DNA
<213> ORGANISM: Zea mays

<400> SEQUENCE: 11
ccgtaccttc cgaagctgca cgcctgcagg taccggtccg gaattcccgg gtcgtatcca      60
cgcgttcggt tagtggtctc aagtgggtcg atgaggtcgt tcccaatgca ccctatgaga    120
taacagaaga attcatgaat actctcttca acaagtacag cattgattac attattcatg    180

-continued

```
gagatgatcc ttgtcttcta cctgatggca ctgatgcata tgcgctagcg aagaaggtcg    240
ggcgttacaa gcaaatcaag cgaacagaag gtgtctcgag cactgacata gttgggagga    300
tattgctaac attcaggcag aaagatgctg acactgattt aagtgttgtc gttgctgaga    360
agtctggaga gaaatcaaat gatgaagtga aaagtcagct atctcatttc cttccaactt    420
ctcgccggat catgcagttt tcaaatgggc aggctccttc gccaggtgct cgtgttgtct    480
atgtagatgg cacatttgat cttttccacg ctggccatgt tgagttcctc aggagtgcca    540
gacaacttgg tgactttctt cttgtgggta tctatgacga cgagtcgatc agggatagaa    600
gaggctgtcg tcctataatg catctccatg agcgtactct ggtgttctt gcctgccgtt    660 atgttgatga agtcattatt ggtgcaccat gggaagtttc taaggacatg atcactacgt    720
ttaacatttc attggttgtc catgggactg tagctgaggg caattcagct ggtgaaattg    780
atccttatgc tgttccaaag agcatgggga ttttccagac aatcaggagc caaaatcta    840 taacaacatt gtcagtggcg acaagaatag ttgacaatcc atgaagctta caagaagagg    900
aacctgaaaa agaaggctag cgaagaccgg tactacacac aaaagaaatt cgtttctgga    960
gactagtgct gcacaaggag tgtatatttc tgccagcagt ccgaggaaat gcatgtgcca   1020
ccctgtattg atgttattct acagcagaga ctggaacaga taatcagcaa tagaaaggtc   1080
acaatgatag tttgagcaat ggtgtggatg gaccaagcta gggaagagag agagagagag   1140
agagagagaa aactgtcaca ttcttctgct gtcgcccttt taggaacgct cacatgacat   1200
gaggagttca cataaacgat tctttttctt tctgactttg ttatccccgt atgggatttt   1260
atatatatct gtagctgaag gccttcagca aaccgttgtt gtatacttgt gtgttgttac   1320
ttaacagcgt gtgtagtgat tagcactgca cactccctga ttgtaccatg gtatattgaa   1380
tgtttatact gctggaagaa aaaaggggg accttgtgat ggtcagatgt ttaatt        1436
```

<210> SEQ ID NO 12
<211> LENGTH: 293
<212> TYPE: PRT
<213> ORGANISM: Zea mays

<400> SEQUENCE: 12

```
Val Pro Ser Glu Ala Ala Arg Leu Gln Val Pro Val Arg Asn Ser Arg
  1               5                  10                  15

Val Val Ser Thr Arg Ser Val Ser Gly Leu Lys Trp Val Asp Glu Val
             20                  25                  30

Val Pro Asn Ala Pro Tyr Glu Ile Thr Glu Glu Phe Met Asn Thr Leu
         35                  40                  45

Phe Asn Lys Tyr Ser Ile Asp Tyr Ile Ile His Gly Asp Asp Pro Cys
     50                  55                  60

Leu Leu Pro Asp Gly Thr Asp Ala Tyr Ala Leu Ala Lys Lys Val Gly
 65                  70                  75                  80

Arg Tyr Lys Gln Ile Lys Arg Thr Glu Gly Val Ser Ser Thr Asp Ile
                 85                  90                  95

Val Gly Arg Ile Leu Leu Thr Phe Arg Gln Lys Asp Ala Asp Thr Asp
            100                 105                 110

Leu Ser Val Val Ala Glu Lys Ser Gly Glu Lys Ser Asn Asp Glu
            115                 120                 125

Val Lys Ser Gln Leu Ser His Phe Leu Pro Thr Ser Arg Arg Ile Met
        130                 135                 140
```

-continued

```
Gln Phe Ser Asn Gly Gln Ala Pro Ser Pro Ala Arg Val Val Tyr
145                 150                 155                 160

Val Asp Gly Thr Phe Asp Leu Phe His Ala Gly His Val Glu Phe Leu
                165                 170                 175

Arg Ser Ala Arg Gln Leu Gly Asp Phe Leu Leu Val Gly Ile Tyr Asp
            180                 185                 190

Asp Glu Ser Ile Arg Asp Arg Arg Gly Cys Arg Pro Ile Met His Leu
        195                 200                 205

His Glu Arg Thr Leu Gly Val Leu Ala Cys Arg Tyr Val Asp Glu Val
    210                 215                 220

Ile Ile Gly Ala Pro Trp Glu Val Ser Lys Asp Met Ile Thr Thr Phe
225                 230                 235                 240

Asn Ile Ser Leu Val Val His Gly Thr Val Ala Glu Gly Asn Ser Ala
                245                 250                 255

Gly Glu Ile Asp Pro Tyr Ala Val Pro Lys Ser Met Gly Ile Phe Gln
            260                 265                 270

Thr Ile Arg Ser Pro Lys Ser Ile Thr Thr Leu Ser Val Ala Thr Arg
        275                 280                 285

Ile Val Asp Asn Pro
    290
```

<210> SEQ ID NO 13
<211> LENGTH: 1947
<212> TYPE: DNA
<213> ORGANISM: Oryza sativa
<220> FEATURE:
<221> NAME/KEY: unsure
<222> LOCATION: (490)
<223> OTHER INFORMATION: n = A, C, G or T

<400> SEQUENCE: 13

```
gcaccagccc gcatctgcca ccctgatctc ctcgcgtcgc gccctcccct cacctcgaat      60
ggcgatacct cctccaccca cgcgcccaa tccctaaccc tagatccctc ctcccacgcc     120
ctctcgcgca cgaccaatct ccctcttcct tcctgttgtg tctctctcgc actgtccaat     180
ctcccaattc attatggagg cggggcggg gagcagcagc gccaagctgg tggcggcgtg     240
cgtcatcggc gggatcgtgc tgggggcatc cgtggtcgcg ctccacctcg ccggcccccgt   300
cgccattccc gccctgcgcc gtcgacgcgc tccgccgcgg ttcgccgcg gacgacggcg     360
ccccgtgcgc gtctacatgg atggctgctt cgacatgatg cactacggcc actgcaacgc    420
gctgcgccag gcgcgcgccc tcggggacga gctcatcgtc ggcgttgtca gcgaccacga    480
gatcaccgcn aacaagggcc cgccggtcac gcccctccac gagaggttga taatggtccg    540
tgctgtaaaa tgggtacacg atgttattcc agatgcacct tacgccataa ctgaggattt    600
catgaataaa ttattcaatg agtataatat agattatatc atccatggcg atgatccttg    660
tctgctccca gatggtactg atgcatatgc tcttgccaaa aaggttggtc gatttaaaca    720
gattaaaaga accgaaggag tgtcaacgac agacattgtt ggaagaatgc ttcttcgtgt    780
tagagagaga tcagcttctg atagtcacaa ccactcttca ctacaaaggc agttcagtca    840
cgggcatggc cagaaaattg atgatagtgg atctgaaagt ggaactagga tatctcatt    900
tcttcctaca tctcggagaa tagttcagtt ctcaaatagc aggggtccag gtccagattc    960
tcggatagtg tacatagatg gtgcatttga tctattccat gctggacatg ttgagatatt   1020
gcgcctcgct cgagagcttg gagatttcct gcttgtgggt attcacacag accagactat   1080
```

-continued

```
aagttcaaca agaggaccac atcgcccaat catgaacctc catgagagaa gtttgagtgt    1140
tttggcttgc cgttatgttg atgaagtgat cattggtgct ccatgggatg tttcgaaaga    1200
tatgattacc acatttaata tttcgttggt tgttcatggg acaattgctg agaatatgga    1260
ctttatgaag gatgatttaa atccatatgc tgttccaagg gctatgggca tctaccgtag    1320
actggagagc cctttagaca tcactactag tactatcata aggaggatag ttgctaacca    1380
tgaagcctac cagaaacgga acgagaagaa agaagccagt gagaagaagt actacgacag    1440
taaaagcttt gtcaatggag agtaacttag gaacaggtct tgcattaatg ctattgccca    1500
gaagtttagt tcacaacctt ctggcacaaa tgcagcggtt agatgatcca caattttaca    1560
gtcttgtggt aactattctc atgttgctga tatagctcag gaaacttcag atgcaaccct    1620
gatgatggtg ctgacttggg tgatgctgga gaccctattt tcctgtatat ggggctttgt    1680
ggctgccaat accagctgtg ttattttgag atgggtagtt ttttttttttt tgttttttttg    1740 ttcaggattg ttgtagagta tgaatgttaa gcttgattaa ctattcctga tgctttattt    1800
cggagttgcc aggtatatgt ggcatcatct tatgagagtc cttttctcat atattttggt    1860
acacttctgt tatgatctgg aactgagcaa ctgatatttg tgtgggtcgg tgacagcaac    1920
tgtgtctgga atctggatgt ttttttcc                                       1947
```

<210> SEQ ID NO 14
<211> LENGTH: 423
<212> TYPE: PRT
<213> ORGANISM: Oryza sativa

<400> SEQUENCE: 14

```
Met Glu Ala Gly Ala Gly Ser Ser Ala Lys Leu Val Ala Ala Cys
 1               5                  10                  15

Val Ile Gly Gly Ile Val Leu Gly Ala Ser Val Ala Leu His Leu
                20                  25                  30

Ala Gly Pro Val Ala Ile Pro Ala Leu Arg Arg Arg Ala Pro Pro
            35                  40                  45

Arg Phe Arg Arg Gly Arg Arg Pro Val Arg Val Tyr Met Asp Gly
        50                  55                  60

Cys Phe Asp Met Met His Tyr Gly His Cys Asn Ala Leu Arg Gln Ala
 65                  70                  75                  80

Arg Ala Leu Gly Asp Glu Leu Ile Val Gly Val Ser Asp His Glu
                85                  90                  95

Ile Thr Ala Asn Lys Gly Pro Pro Val Thr Pro Leu His Glu Arg Leu
            100                 105                 110

Ile Met Val Arg Ala Val Lys Trp Val His Asp Val Ile Pro Asp Ala
        115                 120                 125

Pro Tyr Ala Ile Thr Glu Asp Phe Met Asn Lys Leu Phe Asn Glu Tyr
    130                 135                 140

Asn Ile Asp Tyr Ile Ile His Gly Asp Asp Pro Cys Leu Leu Pro Asp
145                 150                 155                 160

Gly Thr Asp Ala Tyr Ala Leu Ala Lys Lys Val Gly Arg Phe Lys Gln
                165                 170                 175

Ile Lys Arg Thr Glu Gly Val Ser Thr Thr Asp Ile Val Gly Arg Met
            180                 185                 190

Leu Leu Arg Val Arg Glu Arg Ser Ala Ser Asp Ser His Asn His Ser
        195                 200                 205

Ser Leu Gln Arg Gln Phe Ser His Gly His Gly Gln Lys Ile Asp Asp
    210                 215                 220
```

```
Ser Gly Ser Glu Ser Gly Thr Arg Ile Ser His Phe Leu Pro Thr Ser
225                 230                 235                 240

Arg Arg Ile Val Gln Phe Ser Asn Ser Arg Gly Pro Gly Pro Asp Ser
            245                 250                 255

Arg Ile Val Tyr Ile Asp Gly Ala Phe Asp Leu Phe His Ala Gly His
        260                 265                 270

Val Glu Ile Leu Arg Leu Ala Arg Glu Leu Gly Asp Phe Leu Leu Val
    275                 280                 285

Gly Ile His Thr Asp Gln Thr Ile Ser Ser Thr Arg Gly Pro His Arg
290                 295                 300

Pro Ile Met Asn Leu His Glu Arg Ser Leu Ser Val Leu Ala Cys Arg
305                 310                 315                 320

Tyr Val Asp Glu Val Ile Ile Gly Ala Pro Trp Asp Val Ser Lys Asp
                325                 330                 335

Met Ile Thr Thr Phe Asn Ile Ser Leu Val Val His Gly Thr Ile Ala
            340                 345                 350

Glu Asn Met Asp Phe Met Lys Asp Asp Leu Asn Pro Tyr Ala Val Pro
        355                 360                 365

Arg Ala Met Gly Ile Tyr Arg Arg Leu Glu Ser Pro Leu Asp Ile Thr
370                 375                 380

Thr Ser Thr Ile Ile Arg Arg Ile Val Ala Asn His Glu Ala Tyr Gln
385                 390                 395                 400

Lys Arg Asn Glu Lys Lys Glu Ala Ser Glu Lys Lys Tyr Tyr Asp Ser
                405                 410                 415

Lys Ser Phe Val Asn Gly Glu
            420
```

<210> SEQ ID NO 15
<211> LENGTH: 1866
<212> TYPE: DNA
<213> ORGANISM: Glycine max
<220> FEATURE:
<221> NAME/KEY: unsure
<222> LOCATION: (592)
<223> OTHER INFORMATION: n = A, C, G or T
<220> FEATURE:
<221> NAME/KEY: unsure
<222> LOCATION: (613)
<223> OTHER INFORMATION: n = A, C, G or T
<220> FEATURE:
<221> NAME/KEY: unsure
<222> LOCATION: (654)
<223> OTHER INFORMATION: n = A, C, G or T

<400> SEQUENCE: 15

```
gcacgagcat tctacaattc gctacgcatt tcattccatt ccattccatt ttgtgtgggt    60
gctacgaatg aggaaggaga agaagcggtg ctagaataga tagatacata gatagagaag   120
agacatcatc gaacatctcg aaagagaggg aaaatgggta gttacgaggc gttgacggag   180
aagccggcga cggcgacgaa gtgggtggtg acgtgcatgg tgggagggt gatcgtgggg    240 gtgtcactgc tgggtgcata ctcgagccag ctctggaaga gccgaagacg caacaagaag   300
cccgttcgcg tctacatgga tggctgcttt gacatgatgc attatggcca ttgcaatgcc   360
cttcgccaag ctcgtgccct cggcgaccag ttgattgttg gggttgttag tgatgcagag   420
atcattgcca ataagggccc ccccgttacc cctcttcacg aaaggttgat aatggtgaat   480
gcggtgaagt gggtggatga ggttattcct gaagctccct atgcgataac cgaggagttc   540
atgaagaagc ttttgatga gtacaagata gattacatta ttcacgggga tngatccttg   600
```

-continued

```
tgttcttccg gantggaact gatgcttatg ctcatgctaa aaggctggt cgantataag    660 cagataaagc gtactgaagg ggtttccagc actgatattg ttggtcgcat gcttctctgt    720
gtaagagaaa ggtctattac tgaaaaaaat cataatcatt cttctttaca aagacaattc    780
agcaatggcc atagtccgaa gtttgaagct ggtgcatctg ctgcaactgc aagtggaact    840
cgtatatctc attttttgcc tacatctcgt agaattgttc agttctcaaa tgggaggggt    900
ccaggacctg attctcgcat tgtatatata gatggtgctt ttgatctctt tcatgctgga    960
catgttgaga tcttgaggct tgctagggat cttggagatt ttcttcttgt tggaatacac   1020
actgatcaga cagtcagtgc aactagagga tcgcatcgtc ctatcatgaa tcttcatgaa   1080
agaagtctaa gtgttttagc atgtcgctat gtggatgagg ttataattgg tgccccatgg   1140
gagatttcca agatatgct cactacattt aacatctcat tagttgttca tggaaccatt    1200
gcagaaagta atgattttca gaaggaagaa tgcaatccat atgctgttcc tattagcatg   1260
ggcatcttca agttttaga aagtccttta gatataacta ctactacaat aattagaagg    1320
attgtttcaa atcatgaggc ataccagaac cgaaataaga agaagggtga agtgagaaa    1380 agatactacg agggcaagag tcatgtgtct gaagaataat tcatgtctgt cgtttggagc   1440
acagacatag gaggatacca agcttttct ctttttgag aaatgagttt tggttcaact    1500
tggtgcacaa agttggatat tgtgttcagt gcgtctacag gttatgattt gtcaaactta   1560
ttgaaccaac aacttaccta cagttgatca caagtatgaa agcgttcccc aaataaattc   1620
gtgattaact aaattatctg ttaaatgagg tatacttgaa tagactcgcg aaccgaaatg   1680
ttcaacttat gctaccagcc gaacacaact cattttcttc attttttctt ttcttttaaa   1740
tgacctatac tgtattattg ctgtgtgaga agttgttgaa gtattatgtt gtctgattaa   1800
gtattgattt ttttgtttga taaactagtg aaaatatatc cgttaaatga ctattgaata   1860
gttttt                                                             1866
```

<210> SEQ ID NO 16
<211> LENGTH: 421
<212> TYPE: PRT
<213> ORGANISM: Glycine max
<220> FEATURE:
<221> NAME/KEY: UNSURE
<222> LOCATION: (147)
<223> OTHER INFORMATION: Xaa = any amino acid
<220> FEATURE:
<221> NAME/KEY: UNSURE
<222> LOCATION: (154)
<223> OTHER INFORMATION: Xaa = any amino acid
<220> FEATURE:
<221> NAME/KEY: UNSURE
<222> LOCATION: (167)
<223> OTHER INFORMATION: Xaa = any amino acid

<400> SEQUENCE: 16

Met Gly Ser Tyr Glu Ala Leu Thr Glu Lys Pro Ala Thr Ala Thr Lys
 1               5                  10                  15

Trp Val Val Thr Cys Met Val Gly Val Ile Val Gly Val Ser Leu
            20                  25                  30

Leu Gly Ala Tyr Ser Ser Gln Leu Trp Lys Ser Arg Arg Arg Asn Lys
        35                  40                  45

Lys Pro Val Arg Val Tyr Met Asp Gly Cys Phe Asp Met Met His Tyr
    50                  55                  60

Gly His Cys Asn Ala Leu Arg Gln Ala Arg Ala Leu Gly Asp Gln Leu
65                  70                  75                  80

```
Ile Val Gly Val Val Ser Asp Ala Glu Ile Ala Asn Lys Gly Pro
                    85                  90                  95
Pro Val Thr Pro Leu His Glu Arg Leu Ile Met Val Asn Ala Val Lys
                100                 105                 110
Trp Val Asp Glu Val Ile Pro Glu Ala Pro Tyr Ala Ile Thr Glu Glu
            115                 120                 125
Phe Met Lys Lys Leu Phe Asp Glu Tyr Lys Ile Asp Tyr Ile Ile His
        130                 135                 140
Gly Asp Xaa Ser Leu Cys Ser Ser Gly Xaa Glu Leu Met Leu Met Leu
145                 150                 155                 160
Met Leu Arg Arg Leu Val Xaa Tyr Lys Gln Ile Lys Arg Thr Glu Gly
                165                 170                 175
Val Ser Ser Thr Asp Ile Val Gly Arg Met Leu Leu Cys Val Arg Glu
                180                 185                 190
Arg Ser Ile Thr Glu Lys Asn His Asn His Ser Ser Leu Gln Arg Gln
                195                 200                 205
Phe Ser Asn Gly His Ser Pro Lys Phe Glu Ala Gly Ala Ser Ala Ala
            210                 215                 220
Thr Ala Ser Gly Thr Arg Ile Ser His Phe Leu Pro Thr Ser Arg Arg
225                 230                 235                 240
Ile Val Gln Phe Ser Asn Gly Arg Gly Pro Gly Pro Asp Ser Arg Ile
                245                 250                 255
Val Tyr Ile Asp Gly Ala Phe Asp Leu Phe His Ala Gly His Val Glu
                260                 265                 270
Ile Leu Arg Leu Ala Arg Asp Leu Gly Asp Phe Leu Leu Val Gly Ile
                275                 280                 285
His Thr Asp Gln Thr Val Ser Ala Thr Arg Gly Ser His Arg Pro Ile
            290                 295                 300
Met Asn Leu His Glu Arg Ser Leu Ser Val Leu Ala Cys Arg Tyr Val
305                 310                 315                 320
Asp Glu Val Ile Ile Gly Ala Pro Trp Glu Ile Ser Lys Asp Met Leu
                325                 330                 335
Thr Thr Phe Asn Ile Ser Leu Val Val His Gly Thr Ile Ala Glu Ser
            340                 345                 350
Asn Asp Phe Gln Lys Glu Glu Cys Asn Pro Tyr Ala Val Pro Ile Ser
        355                 360                 365
Met Gly Ile Phe Lys Val Leu Gly Ser Pro Leu Asp Ile Thr Thr Thr
        370                 375                 380
Thr Ile Ile Arg Arg Ile Val Ser Asn His Glu Ala Tyr Gln Asn Arg
385                 390                 395                 400
Asn Lys Lys Lys Gly Glu Ser Glu Lys Arg Tyr Tyr Glu Gly Lys Ser
                405                 410                 415
His Val Ser Glu Glu
            420

<210> SEQ ID NO 17
<211> LENGTH: 591
<212> TYPE: DNA
<213> ORGANISM: Triticum aestivum

<400> SEQUENCE: 17
gcacgagaac atgactata  cagaggatga ttcaaatcca tatgctgctc caattgctat    60
gggcatttat cataagctgg atagcccttt ggacatcacc actagtacta ttataaggag   120
```

| | |
|---|---|
| aatagtttct aaccatgaag cctaccagaa acggaatgag aagaaggaag ccagcgagaa | 180 |
| gaagtactat gacagtaaaa gctttgtcaa tggagagtag tgacttctga atagatcttc | 240 |
| tcagaagact gttcctggat cttgaggct ctaacacagg tcacaaatga aaccatcaag | 300 |
| tgatcttcaa ttttaccgct ccattgtcat ttttgctata tagcttagtg cttcagatgc | 360 |
| agtcttgatg catgacaggc agtgctgctg aattgggtgc ggaacctgga tgaatttcca | 420 |
| gtggccactt tcagtgccac tacctaccct atcctcccct gtataccggc ttccagagct | 480 |
| gctgttaccg gccagttct ttttgagatc tatagatctc tgagaattgt ggtacaagat | 540 |
| gaatgctaag gccagttaat tgtttgtttc cctgttgcaa aaaaaaaaa a | 591 |

<210> SEQ ID NO 18
<211> LENGTH: 72
<212> TYPE: PRT
<213> ORGANISM: Triticum aestivum

<400> SEQUENCE: 18

His Glu Asn Met Asp Tyr Thr Glu Asp Asp Ser Asn Pro Tyr Ala Ala
 1               5                  10                  15

Pro Ile Ala Met Gly Ile Tyr His Lys Leu Asp Ser Pro Leu Asp Ile
            20                  25                  30

Thr Thr Ser Thr Ile Ile Arg Arg Ile Val Ser Asn His Glu Ala Tyr
        35                  40                  45

Gln Lys Arg Asn Glu Lys Lys Glu Ala Ser Glu Lys Lys Tyr Tyr Asp
    50                  55                  60

Ser Lys Ser Phe Val Asn Gly Glu
 65                  70

<210> SEQ ID NO 19
<211> LENGTH: 760
<212> TYPE: DNA
<213> ORGANISM: Triticum aestivum

<400> SEQUENCE: 19

| | |
|---|---|
| tgaaaattgg cgttgttaag gtcaagtctg gcattatgga aggtccatct acaaatttga | 60 |
| tcgaatttat cgacttgagt cagaaaagtt ttgccattgc ggctggatcg attttgttta | 120 |
| acccaacatt ctggaatatc gttgcgcgaa aagaatatca tgataagtcc ctaactaaac | 180 |
| ttgctggtgg caatgcacgc tcggctgtt atatactcgc agttaccatc tttttgcttgg | 240 |
| ggatattccg agattttctc tatgagcgcg ccctccgtga tcagcctacc atgccactct | 300 |
| tgttgacaac ccccttcag cttctagccc ttgttttagt tatttcaggc aatatcctag | 360 |
| tcatatcctc aatgtgggcc ctcggaataa ctggtacata ccttggtgat tatttcggaa | 420 |
| ttctaatgga cgaaatggtg acgggcttcc cgtttaatgt taccgacgca cccatgtatt | 480 |
| acggaagcac aatgagtttc ctagggacag cactattctt tggaaagcct gctggaataa | 540 |
| tcttgacaac ggaggttta gttacctaca tgattgcatt gagactggaa atcctttca | 600 |
| cagccaatat ctatgccaag agaggtagca ttgccacgag gccttctcac gagaaagagc | 660 |
| tatagaaatt taaggttgaa taatttctca ttaaacctag ccaaaattag aatttcaatc | 720 |
| tataaattct agctcaataa aaaaaaaaa aaaaaaaaa | 760 |

<210> SEQ ID NO 20
<211> LENGTH: 209
<212> TYPE: PRT
<213> ORGANISM: Triticum aestivum

```
<400> SEQUENCE: 20

Met Glu Gly Pro Ser Thr Asn Leu Ile Glu Phe Ile Asp Leu Ser Gln
 1               5                  10                  15

Lys Ser Phe Ala Ile Ala Ala Gly Ser Ile Leu Phe Asn Pro Thr Phe
            20                  25                  30

Trp Asn Ile Val Ala Arg Lys Glu Tyr His Asp Lys Ser Leu Thr Lys
             35                  40                  45

Leu Ala Gly Gly Asn Ala Arg Leu Gly Cys Tyr Ile Leu Ala Val Thr
         50                  55                  60

Ile Phe Cys Leu Gly Ile Phe Arg Asp Phe Leu Tyr Glu Arg Ala Leu
 65                  70                  75                  80

Arg Asp Gln Pro Thr Met Pro Leu Leu Leu Thr Thr Pro Phe Gln Leu
                 85                  90                  95

Leu Ala Leu Val Leu Val Ile Ser Gly Asn Ile Leu Val Ile Ser Ser
            100                 105                 110

Met Trp Ala Leu Gly Ile Thr Gly Thr Tyr Leu Gly Asp Tyr Phe Gly
        115                 120                 125

Ile Leu Met Asp Glu Met Val Thr Gly Phe Pro Phe Asn Val Thr Asp
        130                 135                 140

Ala Pro Met Tyr Tyr Gly Ser Thr Met Ser Phe Leu Gly Thr Ala Leu
145                 150                 155                 160

Phe Phe Gly Lys Pro Ala Gly Ile Ile Leu Thr Thr Glu Val Leu Val
                165                 170                 175

Thr Tyr Met Ile Ala Leu Arg Leu Glu Asn Pro Phe Thr Ala Asn Ile
            180                 185                 190

Tyr Ala Lys Arg Gly Ser Ile Ala Thr Arg Pro Ser His Glu Lys Glu
        195                 200                 205

Leu
209
```